United States Patent [19]

Bisping

[11] 4,282,885
[45] Aug. 11, 1981

[54] ELECTRODE FOR IMPLANTATION IN THE HEART

[76] Inventor: Hans-Jürgen Bisping, Tittardshang 12, D-5100 Aachen-Laurensberg, Fed. Rep. of Germany

[21] Appl. No.: 935,122

[22] Filed: Aug. 21, 1978

[51] Int. Cl.³ .............................................. A61N 1/04
[52] U.S. Cl. ................................ 128/785; 128/419 P
[58] Field of Search .................... 128/404, 418, 419 P, 128/784, 785, 786

[56] References Cited

U.S. PATENT DOCUMENTS

| 3,416,534 | 12/1968 | Quinn | 128/418 |
|---|---|---|---|
| 3,472,234 | 10/1969 | Tachick | 128/418 |
| 3,737,579 | 6/1973 | Bolduc | 128/418 |
| 3,754,555 | 8/1973 | Schmitt | 128/418 |
| 4,000,745 | 1/1977 | Goldberk | 128/418 |
| 4,106,512 | 8/1978 | Bisping | 128/418 |
| 4,146,036 | 3/1979 | Dutcher et al. | 128/419 P |

FOREIGN PATENT DOCUMENTS

| 2149449 | 4/1972 | Fed. Rep. of Germany . |
|---|---|---|
| 2328966 | 12/1973 | Fed. Rep. of Germany . |
| 2309749 | 9/1974 | Fed. Rep. of Germany . |
| 2319054 | 10/1974 | Fed. Rep. of Germany . |
| 2400549 | 7/1975 | Fed. Rep. of Germany . |

OTHER PUBLICATIONS

Fiandra et al., "American Heart Journal", vol. 91, No. 4, Apr. 1976, pp. 468–474.

Primary Examiner—William E. Kamm
Attorney, Agent, or Firm—Spencer & Kaye

[57] ABSTRACT

Electrode for implantation in the heart, particularly for stimulating the heart muscle, including an electrode lead, a helix protruding at the end of the electrode lead near the heart for screwing the electrode into cardiac tissue, and a protective device protruding beyond the front end of the helix, during insertion of the electrode, against inadvertent hooking-in while the electrode is being inserted through a vein, the device including a cylindrical body which is axially movable within the helix, relative thereto so that it is flush with or protrudes beyond the front end of the helix during the insertion of the electrode and can be removed from the region of the helix which is to be screwed into the tissue by means of an element actuatable from outside of the patient's body in order to fasten the helix in the cardiac tissue.

18 Claims, 7 Drawing Figures

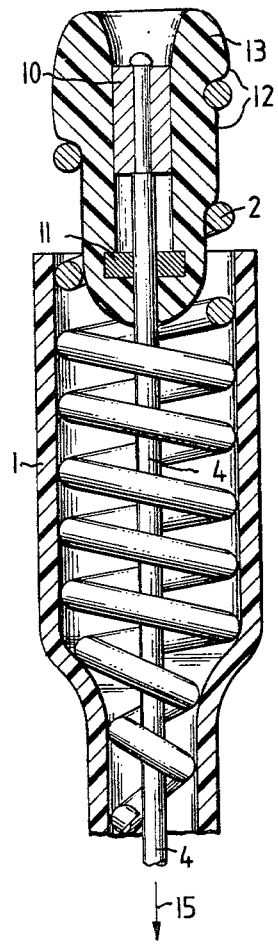
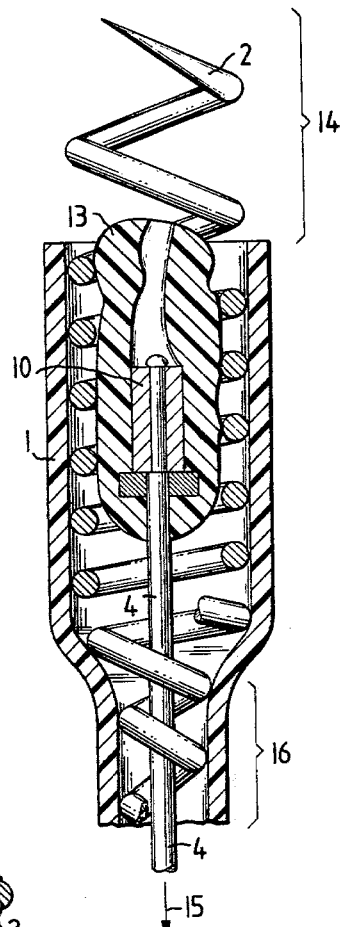
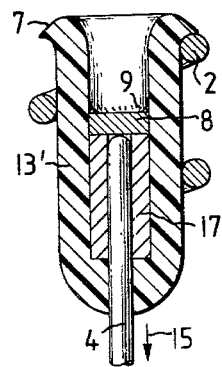

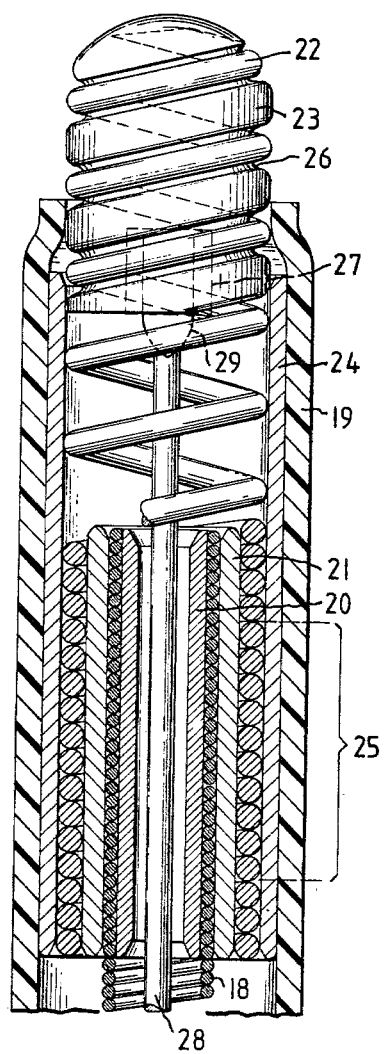
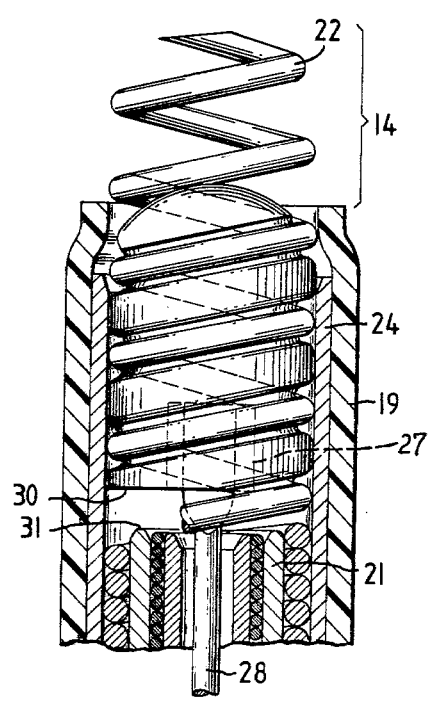

ELECTRODE FOR IMPLANTATION IN THE HEART

BACKGROUND OF THE INVENTION

The present invention relates to an electrode for implantation in the hear, particularly for stimulating the heart muscle, the electrode being of a type which includes an electrode lead, a screw-like protruding helix at the end of the electrode lead near the heart for screwing the electrode into cardiac tissue, and a protective device which protects against inadvertant hooking of the helix and which protrudes over the helix during insertion of the electrode.

Such electrodes serve to transmit stimulation pulses and physiological signals between the heart muscle and a likewise implanted artificial cardiac pacemaker.

It is already known, as disclosed in German Offenlegungsschrift [Laid-Open Application] No. 26 13 044, to protect the helix by means of an elastic cuff which encloses it laterally. If, during the implantation, the electrode end directed toward the heart has been placed at a suitable location within the heart, the exertion of a force in the direction of insertion through the electrode lead and simultaneous rotation of the same, causes the helix to be screwed into the cardiac tissue while the front edge of the cuff rests on the tissue surrounding the point of puncture and is increasingly compressed during the screwing in of the structure so that the part of the helix to be screwed in is progressively exposed. However, for this purpose the electrode lead must be relatively stiff so that it can transmit not only the pressure required to screw in the helix but also the pressure required to compress the cuff. In order to prevent the occurrence of breaks, however, such electrode lead should be as soft as possible.

It is a further drawback that the cuff, once the electrode has been fixed in the heart, continously exerts a force in a direction to cause the screwed-in portion of the electrode head to be pulled out. Moreover, the formation of fibrinous tissue is enhanced so that, as a whole, there is a tendency for the electrode to become ineffective prematurely.

The cuff must also have a certain minimum stiffness since use of a comparatively soft cuff, while it would exert less force when the electrode is in its fastened state, could cause release of the helix during the insertion permitting the helix to possibly become hooked in a vein, or could result, during screwing in of the helix, in entanglement of the cuff with the helix or with the electrode tip, or in hooking of the cuff thereinto, so that this would create a blockage making further screwing in impossible.

A further drawback of the above-metioned electrode is that up to the point of fixation it is caused by the cuff so that it is impossible, before attachment, to establish electrical contact with the cardiac tissue in order to measure the excitation threshold or record an intracardial electrocardiogram.

SUMMARY OF THE INVENTION

It is an object of the present invention to overcome these drawbacks.

A more specific object of the invention is to provide an improved electrode of the above type which assures harmless insertion as well as secure fastening in the cardiac tissue.

A further object of the invention is to make possible performance of electrophysiological measurements before final fixing of the electrode.

These and other objects are accomplished according to the present invention by providing the electrode with a cylindrical body located within the region enclosed by the helix and movable relative thereto in the axial direction so that during insertion of the electrode, the end of the cylindrical body is flush with the tip of the helix or protrudes beyond it and, in order to fasten the helix in cardiac tissue, the cylindrical body can be removed from the region that will be screwed into the tissue by means of an element which can be actuated from outside the patient's body.

The invention is based on the realization that an essentially cylindrical body can be disposed within the portion of the electrode helix which protrudes from the electrode in such a way that the body can be removed from the area of engagement of the helix by a simple movement, such as pulling, screwing or turning. Such movement can be generated by an uncomplicated actuating element which is guided within or outside of the electrode. The cylindrical body can be designed as a protective core and can form a pin that is supported at the helix, and actuation thereof can be effected by a relative force exerted between the actuating element and the electrode without any force acting between the electrode and the tissue surfaces surrounding the region in which the helix is screwed.

In an advantageous manner it is possible to perform stimulation threshold measurements without the helical structure being fastened in the tissue since the present invention allows the turns of the helix to be exposed toward the outside to thereby permit electrical contact with the tissue surface.

The body is driven exclusively via the actuation element by pulling, pressing or rotating the same. The electrode lead may be made of a soft material of the type preferred for such electrode leads since no additional force other than pressure need be applied to remove the protective device when screwing the electrode, and specifically the helix, into the cardiac tissue.

The protective core is advantageously fastened to an actuating strand or wire which is guided along the electrode lead. This strand displaces the cylindrical body accordingly in the axial direction so that during the insertion phase of the electrode it makes the helix ineffective and can be retracted before the helix is screwed into the cardiac tissue.

According to an advantageous embodiment of the invention, the cylindrical body is made, at least in part, of a material impermeable to X-rays, such as platinum, so that the implanting physician will be able to monitor the position of the cylindrical body with respect to the helix at any time via. an X-ray instrument and thus verify that the effective area of the helix has been released for screwing in.

Protection of the helical structure is increased if the front end of the cylindrical body is provided with a circumferential elastic edge, possibly in the form of a lip, which protrudes radially beyond the cylindrical body, and beyond or as far as the effective area of the helix.

According to a modified embodiment of the invention, the cylindrical body may have a tulip shape with a hollow interior which provides particularly favorable possibilities for the configuration of the protective core.

Since the effectiveness of the cylindrical body depends on its guidance within the helix, the body is preferably mounted within the helix essentially without play or is provided with thread-like passages which, in cooperation with the helical pitch of the helix facilitate a screwing process. A "screwdriver" for this purpose is preferably constituted by the appropriately designed guide required to stiffen the electrode during insertion. Since the body advisably extends over several turns of the helix in the longitudinal, or axial, direction, this results in a particularly stable guidance for the relative movement between the helix and the body.

The insertion process is facilitated if the cylindrical body is made convexly rounded in its region which is in the lead during insertion of the electrode.

BRIEF DESCRIPTION OF THE DRAWINGS

FIG. 2 is a view similar to that of FIG. 1 showing the embodiment according to FIG. 1 with the cylindrical body in its retracted position and the helix in a position free to be screwed in.

FIG. 3 is a view similar to that of FIG. 1 of a further embodiment of the electrode according to the invention.

FIG. 4 is a view similar to that of FIG. 1 showing the electrode according to FIG. 3 with the cylindrical body retracted.

FIG. 5 is a cross-sectional detail view of a variation of the cylindrical body for the embodiment of FIGS. 3 and 4.

FIG. 6 is a view similar to that of FIG. 1 of a third embodiment of the invention.

FIG. 7 is a view similar to that of FIG. 1 showing the embodiment of FIG. 6 with the cylindrical body retracted.

DESCRIPTION OF THE PREFERRED EMBODIMENTS

Figure 1:
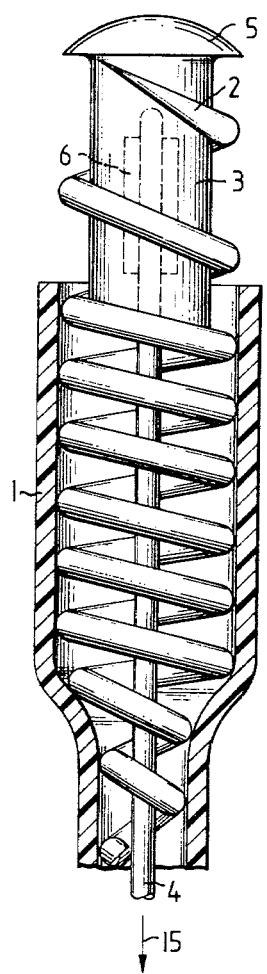
FIG. 1 is a cross-sectional view of the end of an electrode according to a first preferred embodiment of the invention in which the helix can contact the cardiac tissue with the cylindrical body in a position where it protects the helix.
Figure 2:
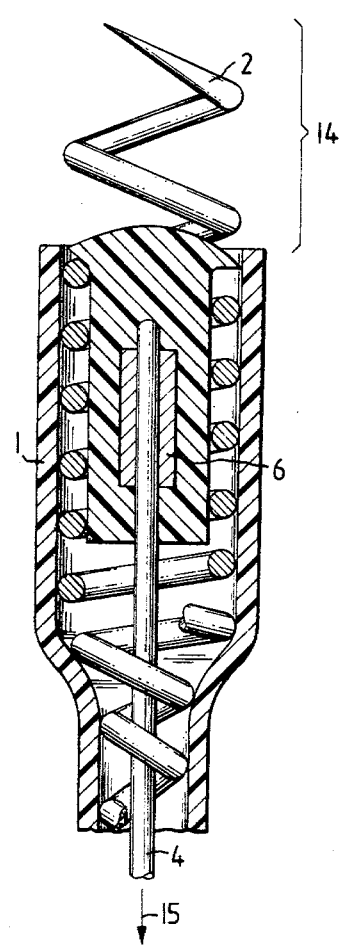

In a first embodiment of the electrode according to the invention, shown in FIGS. 1 and 2, the end of the electrode which extends toward the patient's heart during insertion includes the electrode lead provided with a jacket 1 of flexible material, such as, for example, silicone rubber, that covers part of a helix 2 at the end of the electrode lead. The lead, shown in the drawing in an abbreviated form, is of the length required to connect the heart-side end of the electrode to an implanted cardiac pacemaker, the electrode lead preferably being introduced through a vein. The jacket 1 leaves exposed a corkscrew-shaped portion 14 (FIG. 2) of the helix 2 which is screwed into the cardiac tissue to fasten, or implant, the electrode end. In the illustrated embodiment the portion 14 to be screwed in, in contradistinction to the embodiment to be described below in conjunction with FIGS. 6 and 7, is made of one piece with the portion of the helix 2 forming the lead.

A protective core 3 forming the previously-mentioned cylindrical body is disposed within the helix and is mounted therein to be movable in the axial direction of the helix practically without play. The protective core 3 has a convex curvature at its leading end so as to facilitate insertion of the electrode. An actuating strand or wire 4 is fastened to the protective core 3 and is guided to the other end of the electrode lead outside of the patient's body, so that the physician implanting the electrode can exert a pulling force in the direction of arrow 15 from that end on the protective core 3 to retract it and to remove it from the area 14 of the helix so as to permit fastening of the electrode. The removal of the protective core 3 may also be effected, via a rigid actuating element such as wire, by pushing it out in the opposite direction.

The leading region of the protective core 3, in the direction of insertion of the electrode, protrudes beyond the front end of the helix 2 and is provided with an elastic circumferential rim 5 which extends radially beyond the effective region of the helix 2 so that the tip end of the helix cannot come into engagment with the heart or other body tissue before the protective core 3 is retracted.

The protective core 3 itself is also made of silicone rubber and contains a center 6 (shown in dashed lines in FIG. 1) which is designed as a clamping sleeve to secure the actuating strand 4, is vulcanized into the protective core 3, and is made of a material impermeable to X-rays such as, for example, platin-iridium or ELGILOY.

The presence of the X-ray impermeable center 6 enables the position of the protective core 3 with respect to the helix 2 in the heart to be monitored at any time by means of an X-ray instrument, thus enabling the physician to determine the position of the electrode end as well as the position of the core 3 with respect to the helix 2, i.e. to determine whether the front end of the helix has been completely exposed for screwing the electrode end into the heart wall. In order to effect such release, it is merely necessary to pull at the blocking strand 4 in the direction of the arrow 15 while holding the jacket 1 which encloses the helix 2 in a region of the electrode lead which is outside the patient's body. The protective core 3 then reaches its position shown in FIG. 2, in which, in contradistinction to FIG. 1, the protective core is shown in cross section.

The length of the protective core 3 forming the cylindrical body is selected to assure secure guidance within the helix in the axial, or longitudinal direction. This is accomplished by giving core 3 a length such that it extends over a plurality of turns of the helix 2. The friction force present between the protective core 3 and the helix 2 prevents uncontrolled relative movements of the helix which must be particularly avoided during the insertion process since they might result in a premature release of the screw-in region of the helix.

As is evident, from FIG. 2, the circumferential elastic rim 5 is made to be resilient so that during removal of core 3 from the region 14 of the helix 2 which is to be screwed in, rim 5 can be deformed by pulling on the actuating strand 4 in such a manner that the rim passes the turns of the helix. Only that portion of the elastic rim 5 which intersects the helix at any particular moment is being deformed at any one time, as shown in the left-hand portion of FIG. 2.

FIGS. 3, 4 and 5 show two variations of a second emodiment of the present invention. Here, the cylindrical body is constituted by a silicone rubber core 13 or 13' having a tulip shape and presenting an available interior cavity which permits a particularly good deformability of the regions of the core which engage the helix during removal from the effective region 14 of the helix so that the latter can be screwed into the cardiac tissue.

In the first variation of the seond embodiment, shown in FIGS. 3 and 4, a sleeve 10 is made of ELGILOY, for example, and which is firmly connected with the actuating strand 4 is provided in the interior cavity of the protective core 13 and is clamped around the actuating strand 4. This sleeve 10 is movable in the axial direction in the interior cavity of the tulip-shaped protective core 13. However, the path of travel of the sleeve 10 in the actuation direction of the strand 4 is limited by an abutment ring 11 which is vulcanized into the protective core 13.

For insertion of the electrode, sleeve 10 and protective core 13 are in the positions shown in FIG. 3. The outer lateral surface of protective core 13 is provided with a helical protrusion 12 which is adapted to the portion of helix 2 which is to be screwed in. The turns of the helix are then disposed in grooves between adjacent sides of the protrusion 12 so as to prevent the protective core 13 from being pushed back by the forces exerted during insertion of the electrode at least to the extent that the sharp end of helix 2 cannot go beyond the leading end of the protective core. Sleeve 10 is disposed in the area of the turns which are disposed in the grooves defined by protrusion 12 and prevents elastic inward yielding of the walls of the hollow protective core 13 so that the relative positions of protective core and helix remain the same as long as sleeve 10 is in this position.

In order to screw the effective region 14 of helix 2 into the cardiac tissue, the treating physician pulls at the actuating strand 4 in the direction of the arrow 15, so that the sleeve 10 which is clamped to the strand slides downward inside the protective core 13 until it reaches the abutment ring 11. Then the sleeve 10 begins to act via abutment ring 11 which is made, for example, of polyurethane, to drive the protective core 13 in the direction in which the actuating strand 4 is being pulled. Since the sleeve 10 is no longer in a position to oppose elastic inward deformation of the core wall regions where the effective region 14 of the helix is positioned in the grooves between adjacent sides of protrusion 12, the protective core can undergo a reduction in its cross section and slide downwardly between the turns of helix 2. It then takes on a form as shown in FIG. 4.

The actuating strand 4 can then be pulled via the other end of the electrode until the protective core reaches a subsequent, constricted region 16 of the helix where there exists resistance against further movement in the direction of the arrow 15.

If the sleeve 10 is made of a material which is impermeable to X-rays, the physician will again be able to follow the movement of the sleeve with respect to the helix with the aid of an X-ray instrument.

FIG. 5 shows a modified protective core 13' of tulip shape which has, at its leading end, an elastically deformable circumferential rim 7 that protrudes radially beyond the helix 2 in the region of the frontal plane of the effective region 14. If a force is exerted in the direction of arrow 15 on the actuating strand 4, rim 7 is deformed in the direction toward the interior of the protective core 13' and thus passes by the helix 2. Within the protective core 13' there is disposed an X-ray impermeable center 17, made, for example, of ELGILOY, which is fastened within the protective core 13' in a force fit, is secured to strand 4, and is secured against falling out by wafers 8, made for example, of polyurethane which are fastened by means of an adhesive at 9.

FIGS. 6 and 7 show a further embodiment of the electrode according to the invention, with FIG. 6 showing the leading portion of the electrode in a state ready to be inserted into the vein. In this embodiment, the electrode lead itself is a helical lead 18 which is encased in a silicone rubber tube 19. An internal clamping sleeve 20 is inserted into the interior of the helical lead 18 while the exterior of the helical lead 18 in this region is encased by an intermediate clamping sleeve 21. The actual screw-in helix 22 is wound around the clamping sleeve 21. Around this arrangement there is arranged an external clamping and guide sleeve 24. All of the above-mentioned sleeves and helices are mechanically and electrically connected together in region 25 by pinching or crimping. The material for the sleeves 20, 21 and 24 and helices 18 and 22 is the alloy "Eligiloy". The effective region 14 of the screw-in helix 22 protrudes out of the silicone rubber tube 19.

During the insertion process, a protective core 23 protrudes out of tube 19 to such an extent that its rounded frontal face extends beyond the frontal plane of the screw-in helix 22. The protective core 23 has a circumferential helical groove 26 which forms a thread and has a helical pitch adapted to the pitch of the screw-in helix 22. The outer diameter of the helix 22 decreases helically toward the end near the heart and is thus adapted to the rounded shape of the protective core. In that manner, the tip end of the helix is made inactive during the insertion phase of the electrode and cannot come into engagement with the body tissue.

The core 23 is made of an essentially rigid material, such as, for example, polyurethane. At its end facing the interior of the silicone tube 19 core 23 is provided with a recess 27, shown by broken lines, through which a suitable tool of the type of a combined screw and screwdriver can transmit a torque. The tool for transmitting the torque is a guide wire 28 which has a flattened end 29. This guide wire otherwise serves to impart stiffness to the electrode lead during the insertion process.

Once the electrode has reached the position in which it is supposed to be implanted, the physician is able to make threshold measurements with the protective core, still being in its position for the insertion process, since the extreme portions of the screw-in helix 22 have brought their effective region 14 already into contact with the tissue. If these measurements are not yet satisfactory, the electrode end can be advanced further or retracted at will. If the measuring result is positive, the flat end 29 of the guide wire 28, is fed into recess 27. If the guide wire 28 is than hold fast and the silicone tube 19 with lead 18 in it is rotated by the physician outside of the patients body, the screw-in helix 22 protrudes so that the effective region 14 of the screw-in helix 22 engages with the tissue.

In FIG. 7 the protective core 23 is shown during the retraction process. It can be screwed back in the direction toward the interior of the silicone tube 19 until its rear face 20 comes into contact with the edge 31 of the intermediate clampling sleeve 21. This results in a limitation of movement by way of an abutment so that the physician can sense that the protective core 23 has reached its retracted end position. At the same time, edge 31, which slightly protrudes beyond the corresponding edge of the inner clamping sleeve 20, sealingly contacts rear face 30 so that the interior of the electrode lead is protected against the penetration of body fluids. Then the guide wire 28 is withdrawn.

It will be understood that the above description of the present invention is susceptible to various modifications, changes and adaptations, and the same are intended to be comprehended within the meaning and range of equivalents of the appended claims.

What is claimed is:

1. In an electrode arranged to be inserted into the body of a patient and implanted in the patient's heart, which includes an electrode lead, a structure in the form of a helix protruding at the end of the electrode lead which is directed toward the heart for screwing the electrode into cardiac tissue, and a protective device positioned to protrude beyond the front end of the helix during insertion of the electrode to protect against inadvertent hooling of the helix, the improvement wherein said protective device comprises a cylindrical body disposed within said helix to be axially movable relative to said helix between a protective position in which said body is at least flush with the end of said helix, for insertion of said electrode, and a retracted position in which said helix is exposed for screwing into the cardiac tissue, for performing implantation, said cylindrical body being provided at its outer peripheral surface with shaped regions which are adapted to the pitch of said helix in the manner of threads and which are arranged to come into operating engagement with said helix for preventing movement of said cylindrical body toward its retracted position by forces which are effective thereon during insertion of said electrode, and said electrode comprises an actuating element extending between said cylindrical body and a location outside of the patient's body when said electrode lead is at the implantation location, said actuating element comprising means positively engaging said cylindrical body for driving said cylindrical body in a positive manner from its protective position to its retracted position, by transmitting to said body a retracting force applied to said element at the location outside the patient's body.

2. An arrangement as defined in claim 1 wherein axial movement of said cylindrical body from its protective position to its retracted position, relative to said helix, is in a direction opposite to the direction of insertion of said electrode.

3. An arrangment as defined in claim 1 wherein said cylindrical body has a convexly rounded form in its region which is in the lead during insertion of said electrode.

4. An arrangement as defined in claim 1 wherein said cylindrical body is mounted essentially without play within said helix.

5. An arrangement as defined in claim 1 wherein said cylindrical body is provided, at its end which faces in the electrode insertion direction with an elastic rim which at least in part protrudes beyond the end of said helix when said cylindrical body is in its protective position.

6. An arrangement as defined in claim 5 wherein said cylindrical body is essentially tulip-shaped and is provided with an interior opening extending from the end of said cylindrical body which faces away from its direction of movement into its retracted position.

7. An arrangement as defined in claim 1 wherein said cylindrical body is made to be resilient at its shaped regions so that said regions can move out of operating engagment with said helix, due to deformation of said cylindrical body, during relative movement of said cylindrical body to its retracted position.

8. An arrangement as defined in claim 7 wherein said cylindrical body is provided with an interior passage extending in the direction of movement of said cylindrical body between its said positions, a portion of said passage being located adjacent said shaped regions, and said protective device further comprises a member disposed in said passage for movement therealong to a position in which it is adjacent said shaped regions to oppose deformation of said shaped regions and thereby cause those regions to remain in operative engagement with said helix.

9. An arrangment as defined in claim 8 wherein said actuating element comprises an actuating strand extending adjacent said electrode lead and being fastened to said member for displacing said member in said interior passage to displace said member from its position adjacent said shaped regions.

10. An arrangement as defined in claim 1 wherein said cylindrical body is provided with a recess at its end which faces away from the electrode insertion direction for transmission of a torque to said cylindrical body via said actuating element by means of a form locking connection.

11. An arrangement as defined in claim 10 further comprising a guide wire which serves to reinforce said electrode during the insertion process and which constitutes said actuating element.

12. An arrangement as defined in claim 1 wherein said actuating element comprises an actuating strand extending adjacent said electrode lead.

13. An arrangement as defined in claim 12 wherein said actuating strand is fastened to said cylindrical body.

14. An arrangement as defined in claim 1 wherein said protective device is provided with a portion which is impermeable to X-ray radiation.

15. An arrangement as defined in claim 1 wherein axial movement of said cylindrical body from its protective position to its retracted postion, relative to said helix, is in a direction opposite to the insertion direction, said electrode comprises a member surrounding said electrode lead behind said helix, and said cylindrical body presents a sealing face, at the end thereof facing in the direction of movement into its retracted position, arranged to come into sealing engagement with said member when said cylindrical body moves into its retracted position.

16. An arrangement as defined in claim 1 wherein said electrode serves to stimulate the cardiac muscle.

17. An arrangement as defined in claim 1 wherein the retracting force applied to said element is constituted by an axial pulling force in the direction away from said protective position.

18. An arrangement as defined in claim 1 wherein the retracting force is applied to rotate said cylindrical body to cause it to undergo a helical motion to move into its retracted position.

* * * * *